United States Patent [19]

Dawson

[11] Patent Number: 5,275,803
[45] Date of Patent: Jan. 4, 1994

[54] LIQUID DENTIFRICES

[75] Inventor: Peter L. Dawson, Upton, Great Britain

[73] Assignee: Chesebrough-Pond's USA Co., Greenwich, Conn.

[21] Appl. No.: 891,882

[22] Filed: Jun. 1, 1992

[30] Foreign Application Priority Data

Jun. 4, 1991 [GB] United Kingdom ............... 9112017

[51] Int. Cl.$^5$ ........................... A61K 7/16; A61K 7/18
[52] U.S. Cl. ........................................ 424/52; 424/49
[58] Field of Search ........................................ 424/49–58

[56] References Cited

U.S. PATENT DOCUMENTS

| | | | |
|---|---|---|---|
| 3,935,305 | 1/1976 | Delaney et al. | 424/49 |
| 3,963,832 | 6/1976 | Hashimoto et al. | 424/56 |
| 4,487,757 | 12/1984 | Kiozpeoplov | 424/49 |
| 4,623,536 | 11/1986 | Winston et al. | 424/49 |
| 4,721,614 | 1/1988 | Winston et al. | 424/52 |
| 4,814,160 | 3/1989 | Carter et al. | 424/49 |
| 4,943,429 | 7/1990 | Winston et al. | 424/52 |
| 4,980,153 | 12/1990 | Jackson et al. | 424/52 |
| 5,037,633 | 8/1991 | Ziemkiewicz et al. | 424/49 |
| 5,037,634 | 8/1991 | Williams et al. | 424/49 |
| 5,041,280 | 8/1991 | Smigel | 424/52 |
| 5,085,853 | 2/1992 | Williams et al. | 424/53 |
| 5,089,254 | 2/1992 | Coulson | 424/52 |

FOREIGN PATENT DOCUMENTS 2275191 1/1976 France .

OTHER PUBLICATIONS

Chemical Abstracts, vol. 112, No. 24, Abstract No. 223166R "Manufacturer of Mouthwashes" & JP-A-1 287 015 (Kogyo K.K.), Nov. 17, 1989.

Primary Examiner—Shep K. Rose
Attorney, Agent, or Firm—Milton L. Honig

[57] ABSTRACT

The present invention relates to liquid dentifrices which contain particulate abrasive material, stably suspended in an aqueous vehicle with the aid of a polysaccharide gum as suspending agent. It has been found that high levels of the particulate abrasive material can be stably suspended with less polysaccharide gum than in the prior art, if a small amount of an alkalimetal bicarbonate is included in the dentifrices. This also significantly reduces the loss of available $F^-$ in the dentifrice if a fluorine-containing anticaries agent such as sodium monofluorophosphate is included.

4 Claims, No Drawings

LIQUID DENTIFRICES

FIELD OF THE INVENTION

The present invention relates to liquid dentifrices which contain a particulate abrasive material, stably suspended in a liquid vehicle.

More particularly, it relates to liquid dentifrices which contain at least 20% by weight of a particulate chalk-type abrasive material, stably suspended in an aqueous liquid vehicle with the aid of a polysaccharide gum as suspending agent.

THE RELATED ART

Liquid dentifrices comprising particulate abrasive materials, stably suspended in an aqueous liquid vehicle with the aid of a polysaccharide gum as suspending agent are already known from U.S. Pat. No. 3,506,757 (Salzmann). According to this prior art, particulate abrasive materials can be stably suspended in an aqueous liquid vehicle in an optimum amount of about 10-20% by weight.

However, such a level of particulate abrasive material, particularly if the abrasive material is of the chalk-type, is often insufficient to cleanse the teeth effectively. Increasing the level of chalk in such liquid dentifrices can increase the loss of expensive polymers, particularly if of the Xanthan type, by wasteful chalk-surface adsorption in the absence of suitable chemical competition.

SUMMARY OF THE INVENTION

We have now found that the inclusion of a small amount of an alkalimetal bicarbonate in liquid dentifrice composition of the above type ensures the efficient use of suspending polymer.

Consequently, the present invention relates to a liquid dentifrice which contains a particulate abrasive material of the chalk-type, stably suspended in an aqueous liquid vehicle with the aid of a polysaccharide gum as suspending agent, characterized in that the liquid dentifrice contains more than 20% by weight of the chalk-type abrasive material, and a small amount of an alkalimetal bicarbonate.

As is well-known, the use of chalk-type abrasives in dentifrices that contain a fluorine-containing anticaries agent can lead to a rapid loss of available fluoride ions. This is particularly true for fluorides, and although sodium monofluorophosphate is much more compatible with chalk-type abrasives, in climates with elevated temperatures dentifrices with chalk-type abrasives and sodium monofluorphosphates can also rapidly lose the available fluoride ions. We have now surprisingly found that the inclusion of alkalimetal bicarbonate also significantly reduces such loss of available fluoride ions in the compositions of the invention. A preferred embodiment of our invention is therefore characterised in that the liquid dentifrice further contains an alkalimetal monofluorophosphate.

DETAILED DESCRIPTION

The invention will hereinafter be discussed in more detail. The particulate abrasive material comprises the chalk type materials. These materials include calcium carbonates, both naturally occurring as well as synthetically made. Thus, naturally occurring chalks, limestones and marbles of largely calcitic origin, ground and classified to appropriate particle sizes, e.g. less than 10 micrometer, are very suitable. Dolomites may also be used. Precipitated chalks, made by carbondioxide precipitation of hydrated calcined calcium carbonate minerals, are also very suitable. Owing to their aggregated crystallite structure, larger particles can be used without unduly high Dentine Abrasion Values (DAV's) accruing.

Typical suitable examples are ground limestone of urgonion origin (calcite), classified to a top cut of 7 micrometers, with an average particle size of 1.5 micrometers, and precipitated chalks with a top cut of 20 micrometers and an average particle size of 3-10 micrometers (calcite and aragonite aggregates of primary particle size of about 1-2 micrometers).

Mixtures of various chalk-type materials may also be used. Small amounts of other particulate abrasive materials such as silicas, aluminas, hydroxyapatites, dicalciumphosphates may optionally also be present.

The amount of chalk-type materials in the liquid dentifrice is more than 20% by weight, the upper level being 55%. Preferably the amount ranges from 30-45% by weight.

The aqueous liquid vehicle comprises water, or mixtures of water with an alcohol such as sorbitol, glycerol, ethanol and mixtures thereof. The preferred liquid vehicle consists mainly of water, since the invention enables the manufacture of liquid dentifrices without the use of expensive alcohols such as sorbitol. The aqueous liquid vehicle constitutes in general from 35-70% by weight, preferably from 40-60% by weight of the composition.

The polysaccharide gum which is used as the suspending agent can be any of the well-known polysaccharide gums commonly used in dentifrices. Thus, polysaccharide gums of the Xanthan and Guar types are suitable suspending agents. Of these, the Xanthan gums, either alone or in admixture with Guar type gums are preferred. The Xanthan gums are fully described in U.S. Pat. No. 3,067,038.

In general, the amount of suspending polysaccharide gum in the liquid dentifrice ranges from 0.2-1.5%, preferably from 0.5-0.8% by weight. Other suspending agents may additionally be present in minor amounts, such as smectite clays, pyrogenic silicas, montmorillonites, hectorites, amorphous silicas and sodium carboxymethylcellulose.

The liquid dentifrice furthermore preferably contains a fluoride source as anticaries agent, particularly sodium monofluorophosphate in an amount of 0.5-1.5%, preferably 0.8-1.2% by weight.

The alkalimetal bicarbonate used in the present invention can be sodium, potassium and ammoniumbicarbonate. Sodium carbonate or sesquicarbonate can also be used as a source of bicarbonate, providing the pH of the final composition does not exceed 10. In general, the amount of alkalimetal bicarbonate ranges from 0.1-10%, preferably from 0.5-5% and particularly preferably from 0.5-1% by weight.

The liquid dentifrice of the invention may furthermore contain other optional ingredients, such as anionic, nonionic, zwitterionic and amphoteric surfactants such as soaps, alkylsulphates, alkylbenzene sulphonates, sorbitan esters of fatty acids, sulphobetaines and the like. Flavours, sweeteners, and preservatives may also be included. As preservative formaldehyde is a preferred option, but antimicrobial essential oils containing eugenol, thymol or linalool may also be used as preservative. Other preservatives are benzoic acid esters such as methyl- and propyl parabens®.

Furthermore, the liquid dentifrice may contain other anticaries agents such as casein and casein digests, hydroxyapatites, trimetaphosphates; anti-plaque agents such as zinc citrate, triclosan, copper salts and stannouspyrophosphate; anti-calculus agents such as alkalimetal pyrophosphates; vitamines such as vitamin C, and polymers such as polyvinylmethylether - maleic anhydride copolymers.

The liquid dentifrice of the present invention is formulated such that it exhibits sufficient low stress viscosity to maintain stability, but it must also be strongly shear thinning to aid manufacture and dispensing. It must also show non-thixotropic low shear viscosity characteristics to achieve a satisfactory degree of "brush hold" when dispensed.

Thus, the liquid dentifrice has a typical viscosity of between 50 and 200 Pa.s, preferably 100–150 Pa.s, at a shear rate of 0.1 sec$^{-1}$, though higher viscosities of up to 1500 Pa.s are also possible.

The liquid dentifrice is easy to manufacture in a simple stirred vessel. A preferred order of mixing is
  (i) water
  (ii) abrasive material (+ optional thickening agent)
  (iii) bicarbonate, surfactant, sodium monofluorophosphate
  (iv) polysaccharide gum as a 2–8% aqueous premix
  (v) flavour
  (vi) preservative The invention will further be illustrated by way of the following Examples.

EXAMPLE 1

The following liquid dentifrices were made, using the abovedescribed preferred order of mixing

| | % by weight | | | | | | |
|---|---|---|---|---|---|---|---|
| | I | II | III | IV | V | VI | VII |
| Precipitated chalk A* | 40 | 40 | — | — | — | 30 | 45 |
| Precipitated chalk B** | — | — | 42 | — | — | — | — |
| Ground limestone | — | — | — | 40 | — | — | — |
| Ground marble | — | — | — | — | 38 | — | — |
| Xanthan gum | 0.6 | 0.2 | 0.65 | 0.7 | 0.3 | 0.6 | 0.2 |
| Guar gum | — | 0.4 | — | — | 0.4 | — | 0.4 |
| Thickening silica | — | — | — | — | — | 5 | 7 |
| Sodium monofluorophosphate | 0.8 | 0.8 | 1.2 | 0.8 | 1.2 | 1.0 | 0.8 |
| Sodium bicarbonate | 0.75 | 0.5 | 1.0 | 1.0 | 0.5 | 0.8 | 0.6 |
| Sodium laurylsulphate | 1.5 | 1.0 | — | 1.0 | 1.5 | — | 1.5 |
| Polyxyethylene-sorbitan monooleate | — | — | 1.0 | — | — | 1.5 | — |
| Formalin (40% formaldehyde) | 0.1 | 0.1 | 0.1 | 0.1 | 0.1 | 0.15 | 0.1 |
| Flavour | 0.6 | 1.0 | 1.0 | 1.0 | 1.1 | 0.6 | 1.2 |
| Water | 55.65 | 56.0 | 53.05 | 55.4 | 56.9 | 60.35 | 43.2 |

| | *Pptd chalk A | **Pptd chalk B |
|---|---|---|
| Crystalline form | Calcite (90%) | Aragonite (80%) |
| Top cut (microns) | 10 | 25 |
| Av. particle size (microns) | 5 | 12 |
| Primary part. size (microns) | 1–2 | 2–3 |
| Surface area (m$^2$/g) | 7 | 3 |

Formulations I-VI are liquids, no. VII is pasty. All formulations clean well, deliver fluoride effectively and exhibit DAV's of less than 85.

EXAMPLE 2

An aqueous system comprising 40% by weight of precipitated chalk (average particle size 5 micrometers, primary particle size 1.5 micrometers), 0.6% xanthan gum and 0.8% sodium monofluorophosphate (corresponding to 1,000 ppm F$^-$), with varying amounts of sodium bicarbonate was stored for 12 weeks at 37° C., and the remaining available F$^-$ was determined.

The following results were obtained.

| % sodium bicarbonate | available F$^-$ (ppm) |
|---|---|
| 0 | 600 |
| 0.1 | 600 |
| 0.5 | 680 |
| 1.0 | 850 |
| 5.0 | 915 |

These results show, that the presence of sodium bicarbonate reduces the loss of F$^-$ significantly.

EXAMPLE 3

The following formulations were made:

| | % by weight | | |
|---|---|---|---|
| | a | b | c |
| Precipitated chalk A | 45 | 45 | — |
| Precipitated chalk B | — | — | 45 |
| Sodium bicarbonate | — | 1 | 1 |
| Sodium monofluorophosphate | 0.8 | 0.8 | 0.8 |
| Xanthan gum | 0.25 | 0.25 | — |
| Polyoxyethylene sorbitan monooleate | 1.0 | 1.0 | 1.0 |
| Saccharine | 0.2 | 0.2 | 0.2 |
| Flavour | 1.0 | 1.0 | 1.0 |
| Formalin (40%) | 0.1 | 0.1 | 0.1 |
| Water | 51.6 | 50.6 | 50.9 |

The toothbrush residence time of these dentifrices, and the suspension stability were measured (bulk flow under gravity; separation of solids on storage), and the following results were obtained:

| | a | b | c |
|---|---|---|---|
| Toothbrush residence time (in min.) | 1 | >10 | >10 |
| Stability | unstable | stable | unstable |

These results show, that in the absence of bicarbonate the product is unstable, and has an unacceptable toothbrush residence time (product a), and that in the absence of the polysaccharide gum the product was unstable (product c).

What is claimed is:

1. A liquid dentifrice comprising:
  (i) from more than 20 up to 55% by weight of a particulate chalk-type abrasive material;
  (ii) from 0.1 to 1.5% by weight of a polysaccharide gum for stably suspending the abrasive material in the liquid dentifrice;
  (iii) from 0.1 to 10% by weight of an alkalimetal bicarbonate;
  (iv) from 0.5 to 1.5% by weight of a fluoride source as an anticaries agent; and
  (v) from 35 to 70% by weight of water; wherein the liquid dentifrice has a viscosity between 50 and 1,500 Pa.s at a shear rate of 0.1 sec$^-$ exhibits sufficient low stress viscosity to maintain stability and achieve a satisfactory degree of "brush hold" when dispensed.

2. A liquid dentifrice according to claim 1 wherein the fluoride source is sodium monofluorophosphate present in an amount from 0.8 to 1.2% by weight.

3. A liquid dentifrice according to claim 1 wherein the polysaccharide gum is xanthan gum.

4. A liquid dentifrice according to claim 1 containing from 30–45% by weight of the chalk-type abrasive material, from 0.5–0.8% by weight of the polysaccharide gum, and from 0.5–1 by weight of the alkalimetal bicarbonate.

* * * * *

UNITED STATES PATENT AND TRADEMARK OFFICE
CERTIFICATE OF CORRECTION

PATENT NO. : 5,275,803
DATED : January 4, 1994
INVENTOR(S) : Dawson

It is certified that error appears in the above-indentified patent and that said Letters Patent is hereby corrected as shown below:

On the title page, item (73):

Assignee: "Chesebrough-Pond's USA Co.," should read

-- Chesebrough-Pond's USA Co., Division of Conopco, Inc. --

Signed and Sealed this

Seventh Day of June, 1994

Attest:

BRUCE LEHMAN

*Attesting Officer*     *Commissioner of Patents and Trademarks*